United States Patent [19]

Nussenbaum

[11] Patent Number: 5,465,124
[45] Date of Patent: Nov. 7, 1995

[54] HEADBAND WITH ADJUSTABLE DEVICE FOR POSITIONING AN OPTICAL DEVICE

[75] Inventor: Joseph Nussenbaum, New York, N.Y.

[73] Assignee: Propper Manufacturing Co., Inc., Long Island City, N.Y.

[21] Appl. No.: 257,351

[22] Filed: Jun. 9, 1994

[51] Int. Cl.⁶ .................................................. A61B 3/00
[52] U.S. Cl. ........................... 351/245; 351/155; 359/409
[58] Field of Search ................................. 351/200, 245, 351/158, 140, 155, 205; 2/10, 452; 403/61, 91, 92, 95, 101, 117, 113; 359/409, 410, 411

[56] References Cited

U.S. PATENT DOCUMENTS

| 428,761 | 5/1890 | Sardy | 2/452 |
| 4,538,888 | 9/1985 | Sigelman | 351/245 |
| 4,681,413 | 7/1987 | Schmidt et al. | 351/205 |

OTHER PUBLICATIONS

Advertisement for "The Propper Binocular Indirect Ophthalmoscope" (1991).

*Primary Examiner*—William L. Sikes
*Assistant Examiner*—Huy Mai
*Attorney, Agent, or Firm*—Oppedahl & Larson

[57] ABSTRACT

A positioning device for an optical device is formed of two substantially parallel mounting plates which extend laterally outward from a headband. Each mounting plate has two vertically elongated slots cut in it. The slots closest to the headband (proximal) are in alignment with each other, as are the distal slots on the two mounting plates. Attached to the headband between the two mounting plates is an adjustable stop, such as a threaded rod and nut. The mounting plates and adjustable stop accept an optical device such as an ophthalmoscope having a mounting block affixed to a surface thereof. The mounting block is formed from a body having a hole extending therethrough for receiving a pivot pin. The hole is substantially parallel to the surface of the optical device to which the mounting block is affixed. The mounting block also has two spring loaded balls disposed partially within the body at opposing ends of a line through the body which is parallel to the hole in the body and located below the hole. The mounting block is inserted between the mounting plates, and the pivot pin is inserted through the proximal slot in the first mounting plate, the hole in the body of the mounting block and the proximal slot in the second mounting plate. When fixed to the mounting plates, the position of the mounting block relative to the elongated slots is fixed against unintentional movements by a friction washer or spring. The mounting block pivots into a position resting against the adjustable stop. This position can be changed to accommodate the wearer of the headband. To move the optical device out of the way, the device and mounting block are pivoted upward until the spring loaded balls engage with the distal slots in the mounting plates.

9 Claims, 2 Drawing Sheets 5,465,124

HEADBAND WITH ADJUSTABLE DEVICE FOR POSITIONING AN OPTICAL DEVICE

This application relates to a headband, such as the type of headband employed in ophthalmoscopes, having an adjustable device for positioning an optical device.

Ophthalmologists and other doctors frequently employ optical devices which are supported in position between the eyes of the doctor and the part of the patient being observed by attachment to a headband. This allows the doctor to obtain the benefits of viewing the patient through an optical device while leaving the doctor's hands free. In designing the mechanism by which the optical device is attached to the headband, it is desirable to have a positioning mechanism which allows the doctor to quickly and easily set the correct position of the optical device relative to the headband. It would also be desirable for the optical device to be able to resume this position after having been moved out of the doctor's line of vision.

It is an object of the present invention to provide a headband with an adjustable positioning device which meets these needs.

SUMMARY OF THE INVENTION

These and other objects are achieved in accordance with the present invention using a positioning device which attaches directly to the front of a headband. The positioning device is formed of two substantially parallel mounting plates which extend laterally outward from the head band. Each mounting plate has two vertically elongated slots cut in it. The proximal slots on the two mounting plates, i.e., the slots closest to the headband, are in alignment with each other, as are the distal slots on the two mounting plates. Attached to the headband between the two mounting plates is an adjustable stop, such as a threaded rod and nut.

The mounting plates and adjustable stop accept an optical device such as an ophthalmoscope having a mounting block affixed to a surface thereof. The mounting block comprises a body having a hole extending therethrough for receiving a pivot pin. The hole is substantially parallel to the surface of the optical device to which the mounting block is affixed. The mounting block also has two spring loaded balls disposed partially within the body at opposing ends of a line through the body which is parallel to the hole in the body and located below the hole. The mounting block is inserted between the mounting plates, and the pivot pin is inserted through the proximal slot in the first mounting plate, the hole in the body of the mounting block and the proximal slot in the second mounting plate.

When the mounting block is fixed to the mounting plates, it pivots into a position resting against the adjustable stop. The position of the pivot pin within the proximal slots is maintained against unintentional movement by a friction washer or spring. These positions can be changed to accommodate the wearer of the headband. To move the optical device out of the way, the device and mounting block are pivoted upward until the spring loaded balls engage with the distal slots in the mounting plates. When the optical device is pivoted back downwards, it returns to the same position it previously occupied, because no adjustment of the stop position was necessary to move the device out of the way.

DETAILED DESCRIPTION OF THE INVENTION

Figure 1:
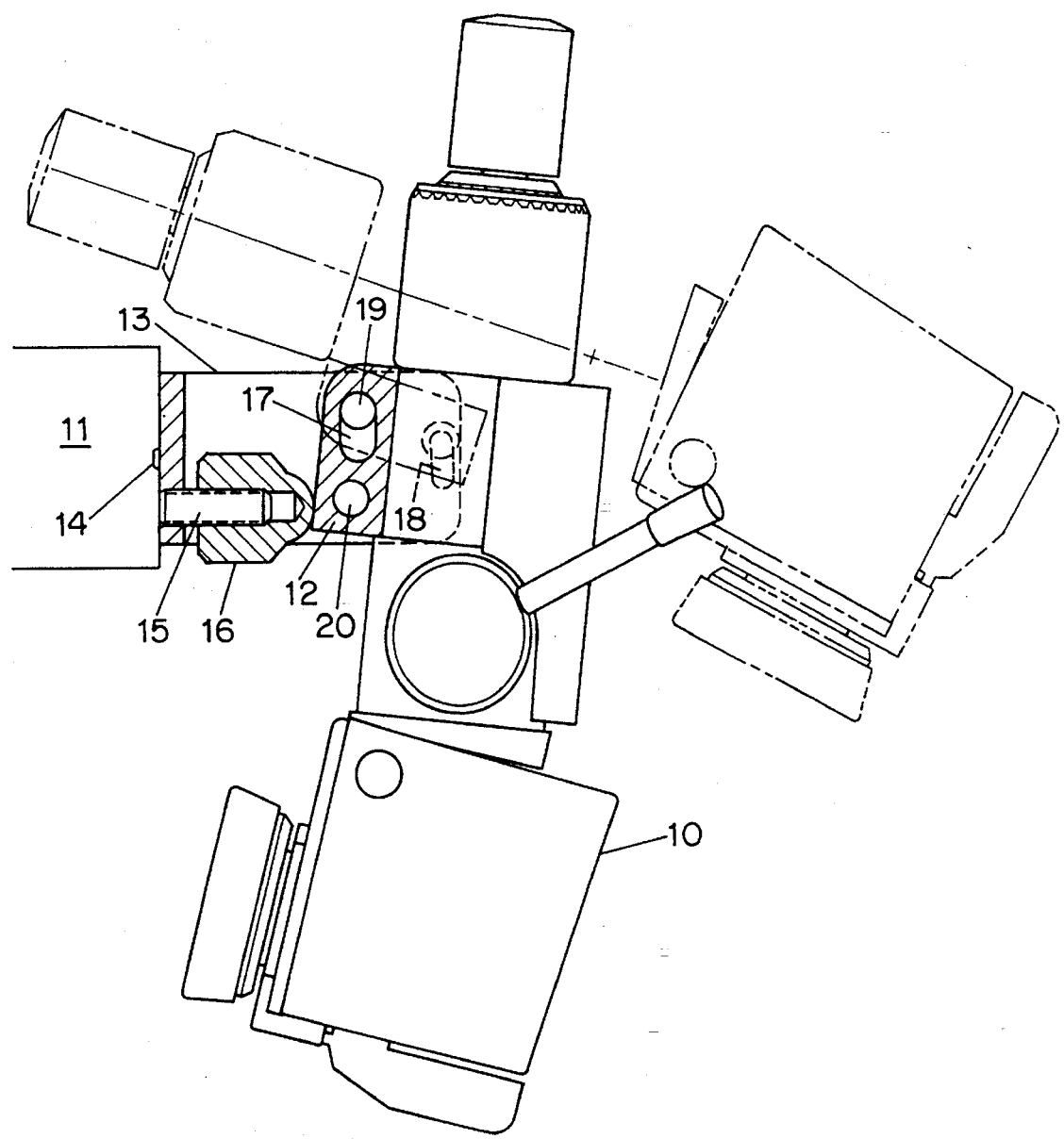
FIG. 1 shows a side view of an apparatus in accordance with the invention.

FIG. 1 shows a side view of an ophthalmoscope 10 mounted to a headband 11 in accordance with the invention. The ophthalmoscope 10 has mounting block 12 affixed to the surface facing the headband. The mounting block has a pair of opposed spring-loaded balls, 20 disposed below a hole for a pivot pin. The headband 11 has a U-shaped bracket 13 affixed to it by a screw 14, with the laterally extending tangs of the U-shaped bracket forming the mounting plates. A threaded rod 15 is affixed to the base of the U-shaped bracket, and accepts a spherical tip nut 16 to form an adjustable stop.

Each of the tangs of the U-shaped bracket 13 has a proximal elongated slot 17 and a distal elongated slot 18. The mounting block 12 is joined to the mounting plates by passing a pivot pin through the proximal slots of the mounting plates and the hole in the mounting block. The position of the pivot pin 19 within the elongated proximal slots 17 is selected by the wearer and maintained against unintentional movements by friction washer 23 placed between the end stop 24 of the pivot pin 19 and one of the mounting plates 13. The ophthalmoscope 10 swings downward around the pivot pin 19 until it rests against the spherical tipped nut 16. Thus, the position of the ophthalmoscope may be adjusted by movement of the nut 16 on the threaded rod 15.

To move the ophthalmoscope out of the way without having to lose this adjustment, the ophthalmoscope 10 is pivoted upwards around the pivot pin 19 until the spring-loaded balls 20 on the mounting block 12 engage with the distal slots 18 in the tangs of the U-shaped bracket 13. The ophthalmoscope in this position is shown in dotted lines in FIG. 1.

Figure 2:
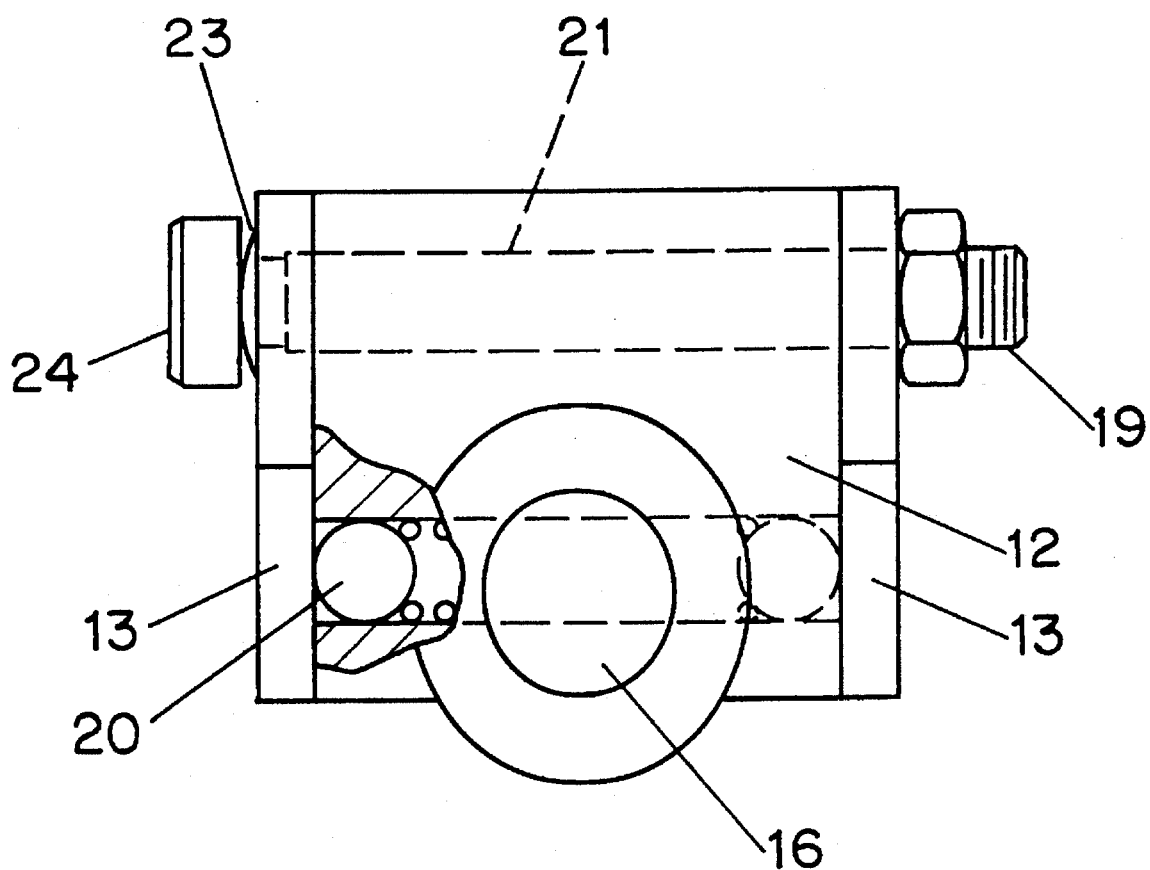
FIG. 2 shows a plan view of the mounting block when used in affixing an optical device to a headband in accordance with the invention.

FIG. 2 shows the mounting block 12 in more detail when viewed from the side facing the headband when in the use position. The pivot pin 19 passes through two tangs of the U-shaped bracket 13 and the hole 21 in the body of the mounting block 12, and is held in place with a nut 22. The spring loaded balls 20 are compressed inwards by the tangs of the U-shaped bracket 13. The position of the spherical tip nut 16 relative to the mounting block 12 is also shown.

While the apparatus shown in FIGS. 1 and 2 represents a preferred form of the invention, it will be apparent to persons skilled in the art that numerous modifications to this specific structure can be made without departing from the spirit of the invention. For example, while a U-shaped bracket is a convenient way of attaching the mounting plates to the headband, it will be apparent that other methods of attaching the mounting plates can also be used. For example, the mounting plates might be formed from separate pieces, such a two L-shaped pieces. Similarly, while the mounting plates are advantageously parallel to each other, it will be understood that deviations from parallel are acceptable, provided that the mounting block can pivot freely between the mounting plates and that the spring-loaded balls can engage the distal slots on the mounting plates. As used in the specification and claims hereof, deviations from parallel which meet these requirements are referred to as being "substantially parallel." Similarly, the adjustable stop may be cam operated rather than affixed to a threaded rod, and a spring might be used in place of friction washer 23 as the means for preventing unintentional sliding of the pivot pin within the proximal elongated slots.

In making the apparatus of the present invention, the various component parts can be fabricated from any dimensionally-stable material. It is desirable to minimize the weight of the apparatus whenever possible, without sacrificing strength. Preferred materials include metals such as aluminum or stainless steel, and plastics such as phenolics.

I claim:

1. An apparatus for positioning an optical device comprising:

(a) a headband;

(b) first and second substantially parallel mounting plates extending laterally outward from a frontal location on the headband, said first and second mounting plates each having proximal and distal vertically elongated slots cut therethrough, said slots in the first mounting plate being in alignment with the slots in the second mounting plate; and (c) adjustable stop means affixed to the headband between the first and second mounting plates.

2. An apparatus according to claim 1, wherein the first and second mounting plates are tangs of a U-shaped bracket.

3. An apparatus according to claim 1, wherein the adjustable stop means comprises a threaded rod extending laterally from the headband, and a nut threaded on the rod.

4. An apparatus according to claim 3, wherein the nut is a spherical tipped nut.

5. An apparatus according to claim 1, further comprising (1) an optical device having a mounting block affixed to a surface thereof, wherein the mounting block comprises a body having a hole extending therethrough for receiving a pivot pin, said hole being substantially parallel to the surface of the optical device to which the mounting block is affixed; and two spring loaded balls disposed partially within the body at opposing ends of a line through the body, said line being parallel to the hole in the body and located below the hole;

(2) a pivot pin, wherein the optical device is attached to the headband by placing the mounting block between the first and second mounting plates and inserting the pivot pin through the proximal slot in the first mounting plate, the hole in the body of the mounting block and proximal slot in the second mounting plate; and (3) means for preventing unintentional sliding of the pivot pin within the proximal slots.

6. An apparatus according to claim 5, wherein the optical device is an ophthalmoscope.

7. An apparatus according to claim 5, wherein the means for preventing unintentional sliding of the pivot pin within the proximal slots is a friction washer.

8. An optical device for attachment to a headband, said optical device having affixed thereto a mounting block comprising:

(a) a body having a hole extending therethrough for receiving a pivot pin, said hole being substantially parallel to the surface of the optical device to which the mounting block is affixed; and (b) two spring loaded balls disposed partially within the body at opposing ends of a line through the body, said line being parallel to the hole in the body and located below the hole.

9. An optical device according to claim 8, wherein the optical device is an ophthalmoscope.

* * * * *